US009125996B2

(12) United States Patent
Takemoto

(10) Patent No.: US 9,125,996 B2
(45) Date of Patent: Sep. 8, 2015

(54) LIQUID INJECTION INSTRUMENT

(75) Inventor: Masafumi Takemoto, Shizuoka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 26 days.

(21) Appl. No.: 14/009,900

(22) PCT Filed: Apr. 4, 2012

(86) PCT No.: PCT/JP2012/059159
§ 371 (c)(1),
(2), (4) Date: Oct. 4, 2013

(87) PCT Pub. No.: WO2012/137803
PCT Pub. Date: Oct. 11, 2012

(65) Prior Publication Data
US 2014/0025006 A1 Jan. 23, 2014

(30) Foreign Application Priority Data

Apr. 7, 2011 (JP) ................................ 2011-085839

(51) Int. Cl.
*A61M 5/32* (2006.01)
*A61M 5/20* (2006.01)

(52) U.S. Cl.
CPC ........... *A61M 5/3245* (2013.01); *A61M 5/2033* (2013.01); *A61M 5/3204* (2013.01); *A61M 2005/2013* (2013.01); *A61M 2005/3247* (2013.01); *A61M 2005/3267* (2013.01)

(58) Field of Classification Search
CPC ............ A61M 5/2033; A61M 5/2343; A61M 5/3245; A61M 5/3257; A61M 5/326; A61M 2005/3247; A61M 2005/3267; A61M 5/3243; A61M 2005/2013

USPC .......................... 604/134, 135, 137, 197, 198
See application file for complete search history.

(56) References Cited

U.S. PATENT DOCUMENTS

| 2005/0033230 A1 | 2/2005 | Alchas et al. | |
|---|---|---|---|
| 2007/0129686 A1* | 6/2007 | Daily et al. | 604/192 |
| 2009/0312705 A1* | 12/2009 | Grunhut et al. | 604/110 |

(Continued)

FOREIGN PATENT DOCUMENTS

| JP | 2005-500871 | 1/2005 |
|---|---|---|
| JP | 2009-533124 | 9/2009 |

(Continued)

OTHER PUBLICATIONS

International Search Report, mail date is May 29, 2012.

*Primary Examiner* — Kami A Bosworth
(74) *Attorney, Agent, or Firm* — Greenblum & Bernstein, P.L.C.

(57) ABSTRACT

A liquid injection instrument includes an internal structural body having a cylindrical body that has a cylindrical shape and has an inner cavity part in which a drug solution is housed, a hollow needle disposed at a distal part of the cylindrical body, a gasket slidable in the cylindrical body, and a plunger that carries out movement operation of the gasket along an axial direction of the cylindrical body. The liquid injection instrument further includes a cylindrical protector disposed on an outer circumferential side of the internal structural body movably along the axial direction of the internal structural body. The protector has an outside engagement piece and the cylindrical body has an inside engagement piece engageable with the outside engagement piece.

9 Claims, 11 Drawing Sheets

(56) References Cited

U.S. PATENT DOCUMENTS

2010/0121272 A1 5/2010 Marshall et al.
2010/0280460 A1 11/2010 Markussen
2013/0310758 A1* 11/2013 Wozencroft ................. 604/197

FOREIGN PATENT DOCUMENTS

| JP | 2010-532243 | 10/2010 |
| WO | 2010/136076 | 12/2010 |

* cited by examiner

LIQUID INJECTION INSTRUMENT

TECHNICAL FIELD

The present invention relates to a liquid injection instrument.

BACKGROUND ART

When a drug solution is administered to a patient for example, a blood vessel of the patient is punctured by a hollow needle to perform it. As a medical instrument by which such a procedure can be carried out, one is known that has a syringe unit composed of a cylindrical body in which a drug solution is filled and a hollow needle mounted at a distal part of the cylindrical body, a cylindrical casing that houses the syringe unit movably, and an operation button that is provided at a proximal part of the casing and is to carry out start operation of actuation of the syringe unit (for example, refer to Patent Document 1). In the medical instrument described in this Patent Document 1, the syringe unit can move to a first position at which the hollow needle protrudes from a distal opening of the casing and a second position at which the hollow needle is retracted to a position closer to a proximal side than the distal opening of the casing.

However, in the medical instrument described in Patent Document 1, although the syringe unit returns to the second position after use thereof, possibly this syringe unit unintentionally moves to the first position because being not surely fixed at the second position. In this case, there is a problem that a hand finger or the like is accidentally punctured by the protruding hollow needle.

Furthermore, when a drug solution is administered by using the medical instrument described in Patent Document 1, the casing needs to be grasped and a pressing operation of a syringe button needs to be carried out with the casing grasped. Therefore, corresponding to the existence of the syringe button, a structure of this medical instrument is complicated, which possibly causes failure. Moreover, in the pressing operation of the syringe button, the user is caused to feel fear at the time of the use by operation sound and movement sound of the syringe unit or e.g. difficulty in grasping what movement speed the syringe unit moves at for puncturing by the hollow needle, so that the user hesitates to use it. That is, there is also a problem that this medical instrument is inferior in the operability.

Patent Document 1: JP-T-2010-532243

DISCLOSURE OF INVENTION

An object of the present invention is to provide a liquid injection instrument that has a simple structure and is excellent in the operability of liquid injection operation (particularly prevention of accidental puncturing after use).

To achieve the above-described object, the present invention is a liquid injection instrument including
an internal structural body having
 a cylindrical body that has a cylindrical shape and has an inner cavity part in which a liquid is housed,
 a hollow needle that is disposed at a distal part of the cylindrical body, communicates with the cylindrical body, and has a sharp needle tip at a distal end,
 a gasket that is slidable in the cylindrical body, and
 a plunger that is coupled to the gasket and carries out a movement operation of the gasket along an axial direction of the cylindrical body; and
 a protector that is disposed on an outer circumferential side of the internal structural body movably relative to the internal structural body along the axial direction, and has a tubular shape and a distal opening;
wherein the protector is capable of taking
 a first state in which the liquid still remains housed in the cylindrical body and the distal opening of the protector is located closer to a distal side than the needle tip,
 a second state in which the needle tip protrudes from the distal opening of the protector due to a movement of the protector toward a proximal side and the gasket is movable in a distal direction,
a third state in which the liquid is discharged via the hollow needle due to a movement of the gasket in the distal direction, and
 a fourth state in which the distal opening of the protector is located closer to the distal side than the needle tip again,
 wherein the protector has an outside engagement piece that is provided in a tube wall of the protector and is elastically deformed,
 the cylindrical body has an inside engagement piece that is provided at a proximal part of the cylindrical body, engages with the outside engagement piece in the fourth state, and is elastically deformed, and
 the plunger has a pressing portion that presses and deforms the inside engagement piece outward in the fourth state, and
 wherein in the fourth state, the inside engagement piece is pressed outward by the pressing portion to engage with the outside engagement piece, so that the movement of the protector in a proximal direction is prohibited by the engagement.

Furthermore, in the liquid injection instrument of the present invention, it is preferable that the protector has a slit having a U-shape in a side view of the protector, the slit is formed in the tube wall of the protector, and a part surrounded by the slit functions as the outside engagement piece.

In addition, in the liquid injection instrument of the present invention, it is preferable that the inside engagement piece is so formed as to protrude in the proximal direction at the proximal part of the cylindrical body and has a claw that is so formed as to protrude outward at a proximal end of the inside engagement piece, and wherein the claw engages with the outside engagement piece.

Moreover, in the liquid injection instrument of the present invention, it is preferable that the plunger is formed of an elongated member, and
 wherein the pressing portion is a part that is so formed as to protrude in the middle of an axial direction of the plunger, and has an inclined surface that is so inclined that a distance from an axis of the plunger gradually increases in the proximal direction.

Furthermore, in the liquid injection instrument of the present invention, it is preferable to further include restricting means that restricts a movement of the plunger in the distal direction in the first state and releases the restriction on the plunger in the second state.

In addition, in the liquid injection instrument of the present invention, it is preferable that the plunger is formed of an elongated member,
 wherein the restricting means has
 a protrusion that is so formed as to protrude at a position different from a position of the pressing portion in the middle of an axial direction of the plunger,
 a first restricting member that is provided fixedly to the cylindrical body and includes an elastic piece elastically deformed in such a manner as to be capable of getting close to/away from the protrusion, and a second restricting member that moves to a restriction position at which the elastic piece gets close to and engages with the protrusion and the engagement state is kept, and moves from the restriction position to a release position at which the elastic piece is capable of getting away from the protrusion, and wherein the second restricting member is located at the restriction position in the first state, and moves to the release position in association with the movement of the protector in the proximal direction in transition to the second state.

Moreover, in the liquid injection instrument of the present invention, it is preferable to further include a first biasing member that biases the gasket in the distal direction via the plunger in the third state, wherein a biasing force of the first biasing member is set to such a magnitude as to release the engagement between the elastic piece and the protrusion when the second restricting member exists at the release position.

Furthermore, in the liquid injection instrument of the present invention, it is preferable to further include a second biasing member that biases the protector in the distal direction so that the distal opening of the protector is located closer to the distal side than the needle tip in the first state, and biases the protector in the distal direction so that the distal opening of the protector is located closer to the distal side than the needle tip again in transition to the fourth state.

In addition, in the liquid injection instrument of the present invention, it is preferable to further include a cylindrical grip member that has a cylindrical shape and a distal opening, and is disposed concentrically with the protector, wherein the grip member fixedly supports, inside the grip member, the internal structural body in such a manner that the needle tip protrudes from the distal opening of the grip member, and the grip member supports the protector movably relative to the internal structure body along the axial direction.

BEST MODES FOR CARRYING OUT THE INVENTION

A liquid injection instrument of the present invention will be described in detail below based on a preferred embodiment shown in the accompanying drawings.

Figure 4:
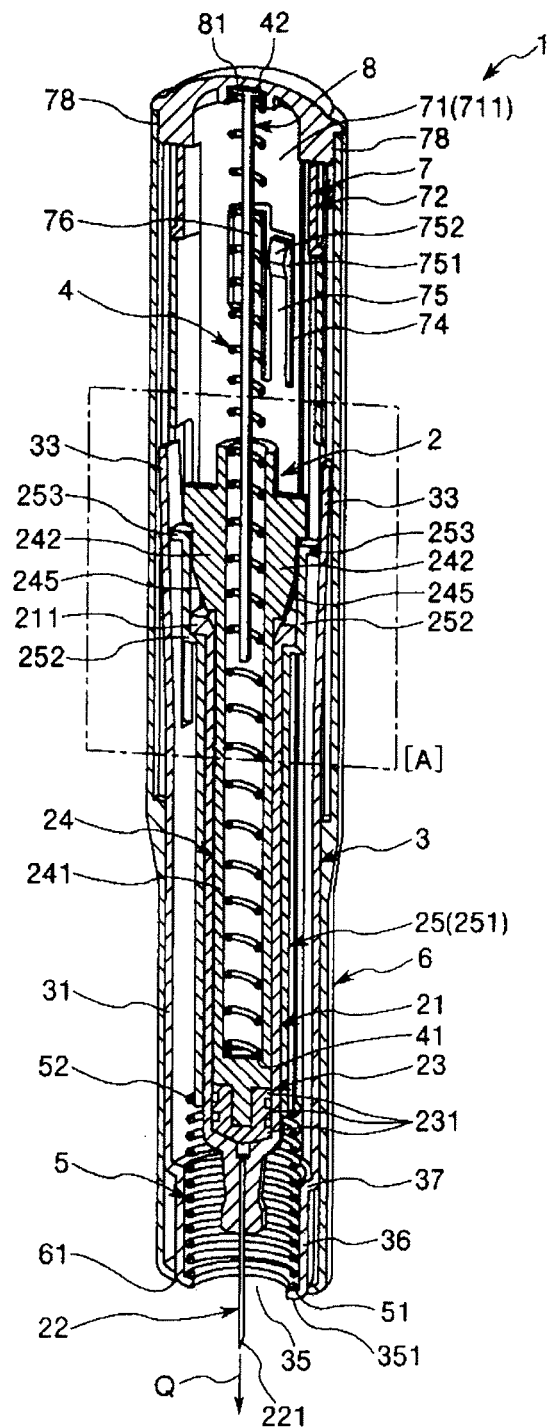
FIG. 4 is a longitudinal-sectional perspective view sequentially showing the actuation state of the liquid injection instrument of the present invention.
Figure 5:
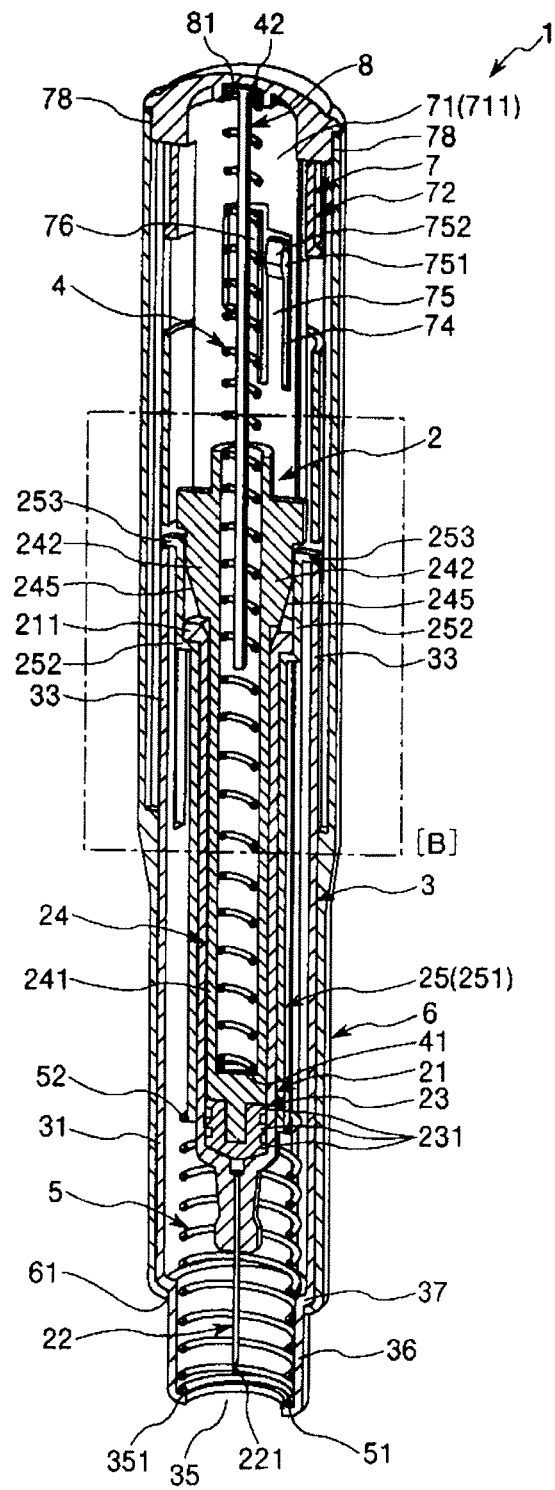
FIG. 5 is a longitudinal-sectional perspective view sequentially showing the actuation state of the liquid injection instrument of the present invention.
Figure 6:
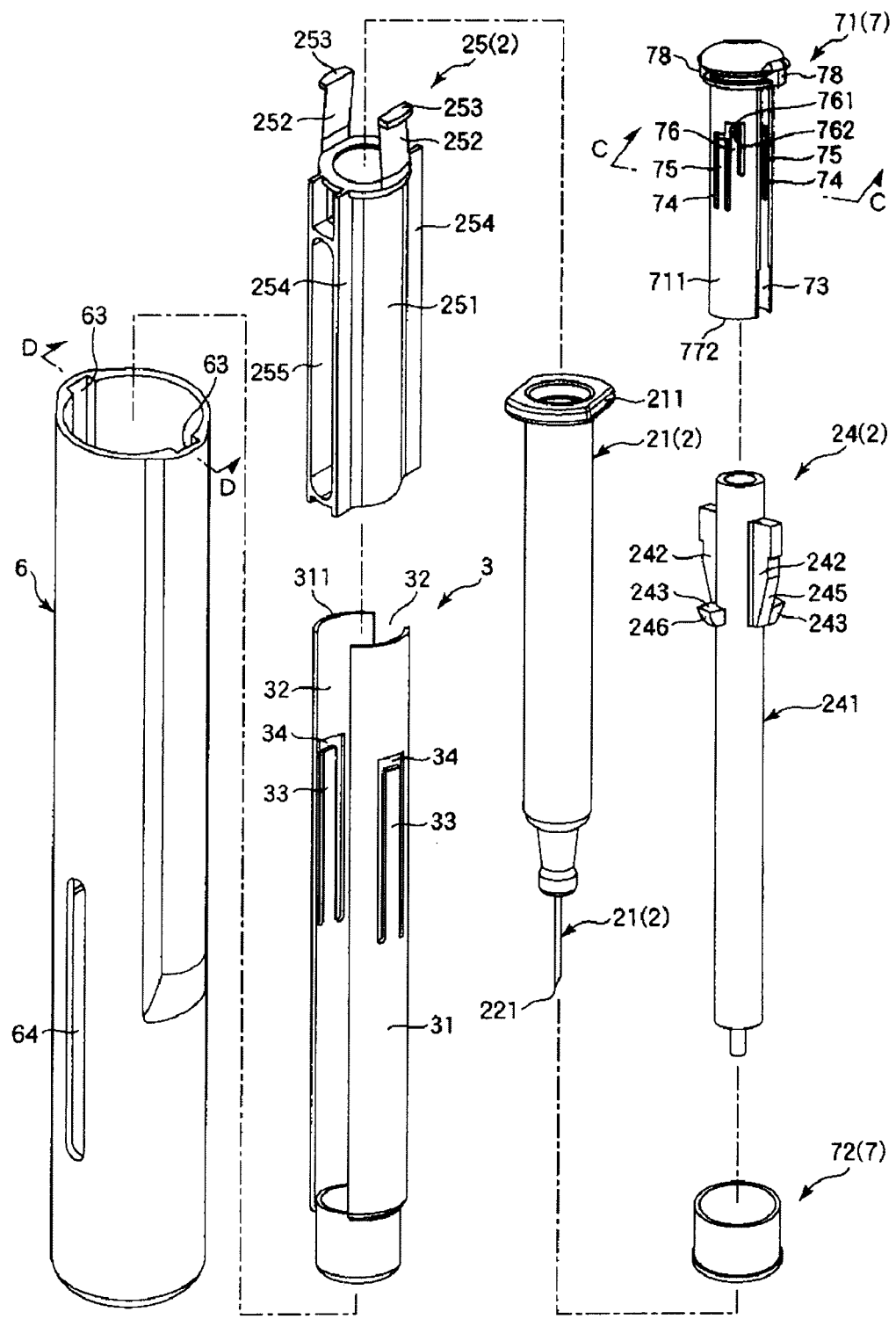
FIG. 6 is an exploded perspective view showing a part of an internal structure of the liquid injection instrument shown in FIGS. 1 to 5.
Figure 7:
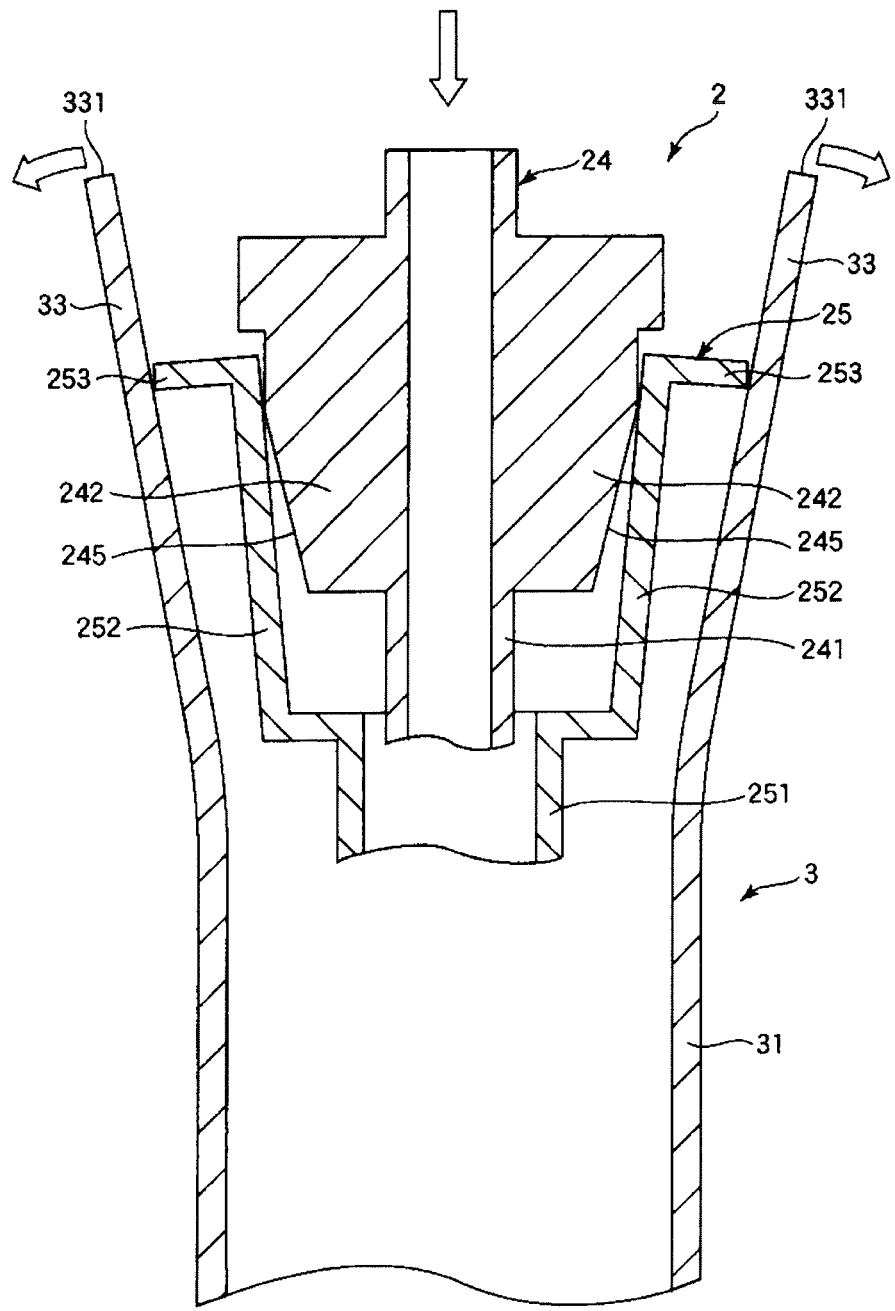
FIG. 7 is a detail view of an area [A] surrounded by a one-dot chain line in FIG. 4.
Figure 8:
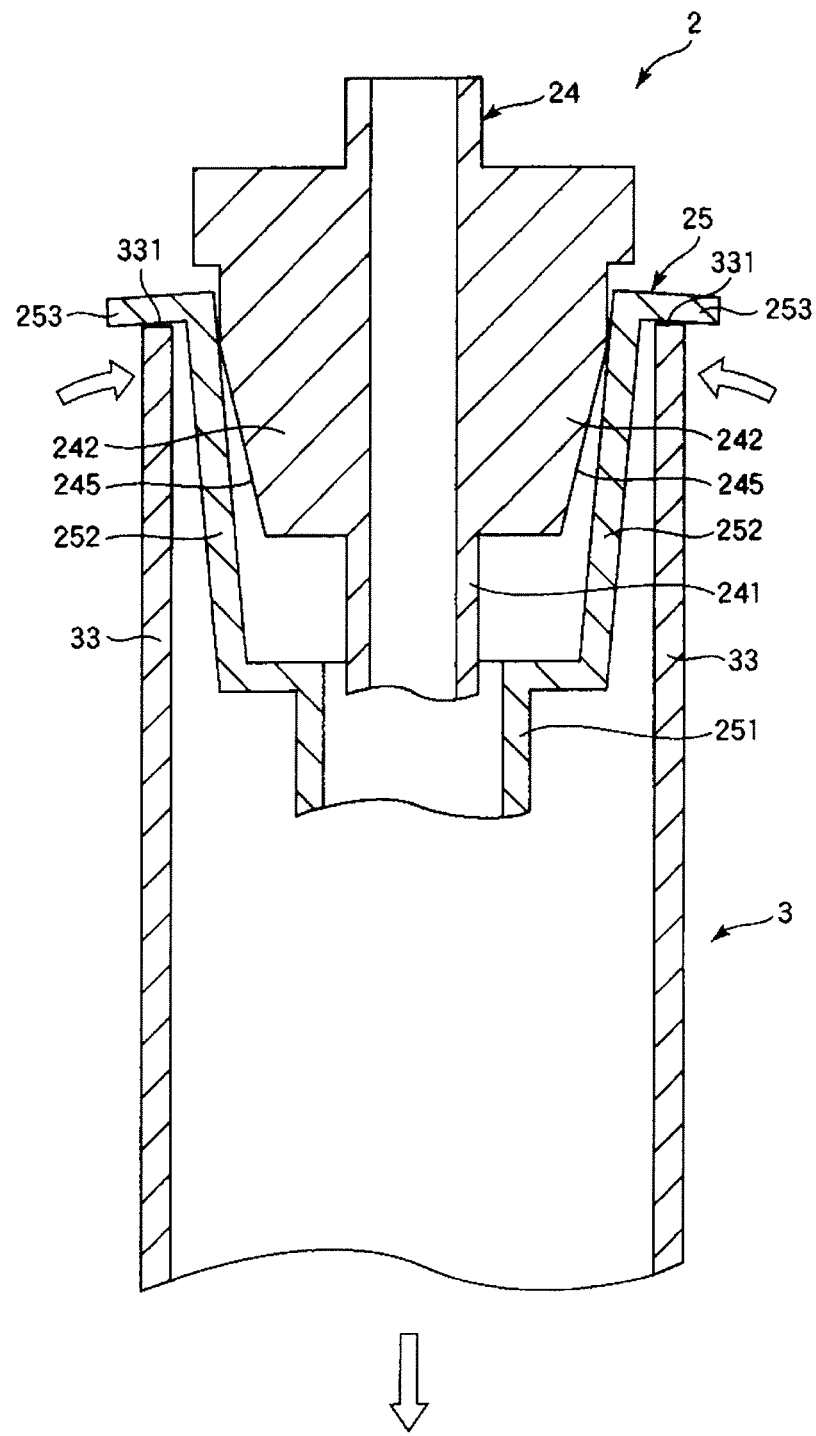
FIG. 8 is a detail view of an area [B] surrounded by a one-dot chain line in FIG. 5.
Figure 9:
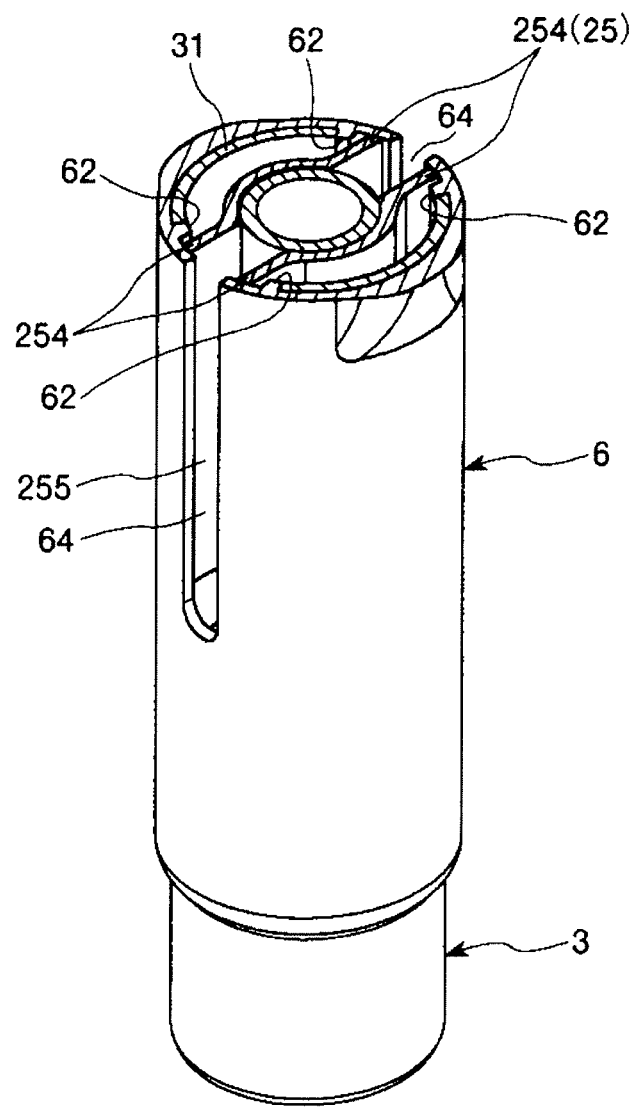
FIG. 9 is a cross-sectional perspective view showing a state in which an engagement member, a protector, and a grip member in FIG. 6 are assembled.
Figure 10:
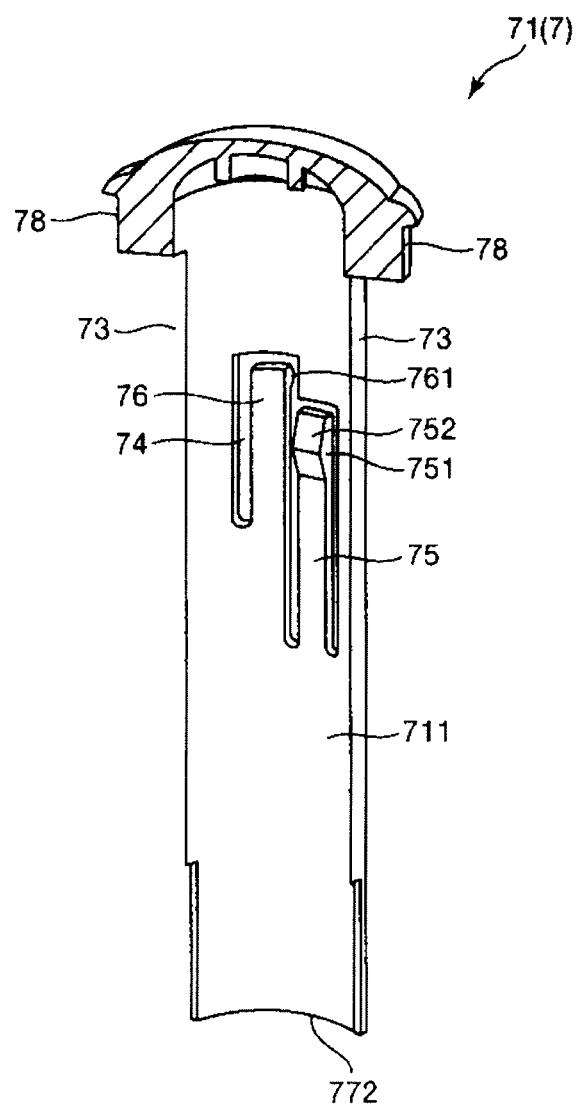
FIG. 10 is a sectional view along the line C-C in FIG. 6.
Figure 11:
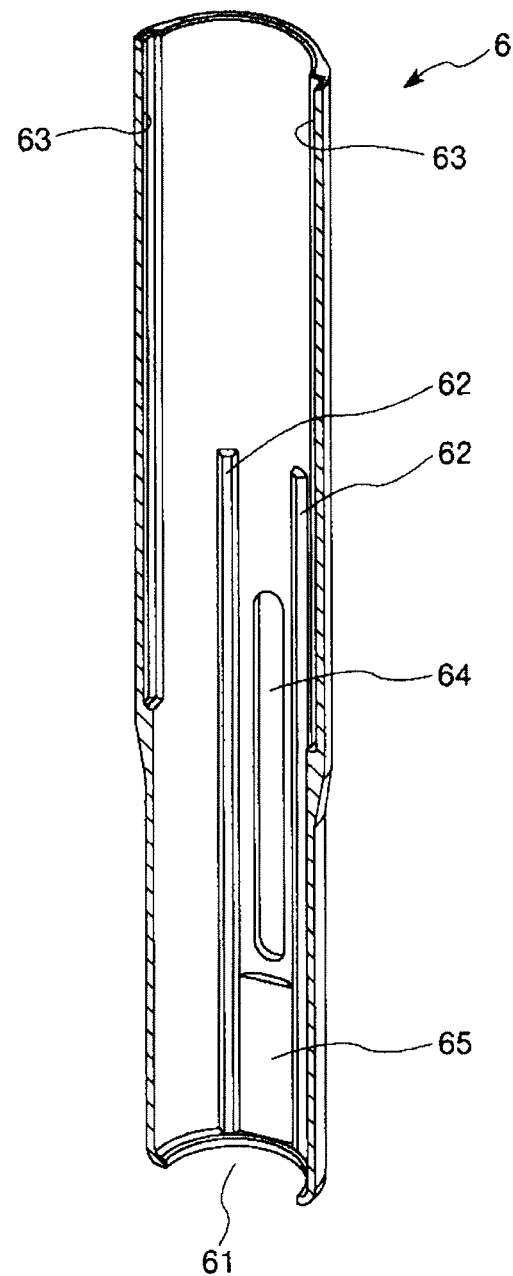
FIG. 11 is a sectional view along the line D-D in FIG. 6.

FIGS. 1 to 5 are each a longitudinal-sectional perspective view sequentially showing an actuation state of a liquid injection instrument of the present invention. FIG. 6 is an exploded perspective view showing a part of an internal structure of the liquid injection instrument shown in FIGS. 1 to 5. FIG. 7 is a detail view of an area [A] surrounded by a one-dot chain line in FIG. 4. FIG. 8 is a detail view of an area [B] surrounded by a one-dot chain line in FIG. 5. FIG. 9 is a cross-sectional perspective view showing a state in which an engagement member, a protector, and a grip member in FIG. 6 are assembled. FIG. 10 is a sectional view along the line C-C in FIG. 6. FIG. 11 is a sectional view along the line D-D in FIG. 6. Hereinafter, the upper side in each of FIGS. 1 to 10 will be expressed as "proximal" and the lower side will be expressed as "distal" for convenience of explanation.

A liquid injection instrument 1 shown in FIGS. 1 to 5 is a syringe in which a drug solution (liquid) Q is filled in advance and is used when the drug solution Q is injected (administered) to a living body. The drug solution Q is arbitrarily selected according to the use purpose thereof and examples thereof mainly include drug solutions to be subcutaneously injected, such as a hematinic, a vaccine, a hormone preparation, an antirheumatic drug, an anticancer drug, an anesthetic, and an anticoagulant.

This liquid injection instrument 1 includes an internal structural body 2, a protector 3 disposed movably relative to the internal structural body 2, a coil spring 4 as a first biasing member, a coil spring 5 as a second biasing member, a grip member 6 grasped when the liquid injection instrument 1 is used, and restricting means 7. The configurations of the respective parts will be described below.

As shown in FIGS. 1 to 5, the internal structural body 2 has a cylindrical body 21 having a bottomed cylindrical shape, a hollow needle 22 disposed at a distal part of the cylindrical body 21, a gasket 23 slidable in the cylindrical body 21, a plunger 24 coupled to the gasket 23, and a cylindrical engagement member 25 covering an outer circumferential part of the cylindrical body 21.

The cylindrical body 21 can house the drug solution Q in its inner cavity part, i.e. in a space surrounded by the cylindrical body 21 and the gasket 23. A plate-shaped flange 211 is so formed as to protrude at a proximal outer circumferential part of the cylindrical body 21.

Furthermore, on the outer circumferential part of the cylindrical body 21, the engagement member 25 having two inside engagement pieces 252 is mounted.

The engagement member 25 has a cylindrical portion 251 covering the outer circumferential part of the cylindrical body 21. The flange 211 of the cylindrical body 21 is locked on a proximal surface of this cylindrical portion 251. This prevents separation of the cylindrical body 21 from the engagement member 25 in the distal direction.

At a rim part of a proximal opening part of the cylindrical portion 251, the two inside engagement pieces 252 are each so formed as to protrude in the proximal direction. These inside engagement pieces 252 are disposed opposed to each other through the axis of the cylindrical portion 251. Furthermore, the inside engagement pieces 252 can be elastically deformed in such a manner as to be capable of getting close to/away from each other.

Moreover, the inside engagement pieces 252 each have, at its proximal end, claws 253 that are so formed as to protrude outward. Each claw 253 is located closer to a proximal side than the flange 211 of the cylindrical body 21. As shown in FIG. 8, these claws 253 are a part that engages with outside engagement pieces 33 of the protector 3.

Guide portions 254 having an elongated shape are so formed as to protrude on the outer circumferential part of the cylindrical portion 251.

A constituent material of each of the cylindrical body 21, the plunger 24, and the engagement member 25 is not particularly limited. Examples thereof include various kinds of resins such as polyvinyl chloride, polyethylene, polypropylene, cyclic polyolefin, polystyrene, poly-(4-methylpentene-1), polycarbonate, an acrylic resin, an acrylonitrile-butadiene-styrene copolymer, polyester typified by polyethylene terephthalate and polyethylene naphthalate, a butadiene-styrene copolymer, and polyamide (e.g. Nylon 6, Nylon 6.6, Nylon 6.10, Nylon 12). Among them, the resins such as polypropylene, cyclic polyolefin, polyester, and poly-(4-methylpentene-1) are preferable in that shaping is easy.

The cylindrical body 21 and the engagement member 25 may be made as one cylindrical body by being integrally formed.

The hollow needle 22 is fixed at a bottom part (distal part) of the cylindrical body 21. This hollow needle 22 communicates with the inner cavity part of the cylindrical body 21 and can discharge the drug solution Q filled in this inner cavity part.

Furthermore, a sharp needle tip 221 is formed at a tip of the hollow needle 22. A living body surface can be punctured by the needle tip 221 and the drug solution Q can be administered to the living body via the hollow needle 22 in this punctured state.

The hollow needle 22 is formed of e.g. a metal material such as stainless steel, aluminum or aluminum alloy, or titanium or titanium alloy.

In the cylindrical body 21, the gasket 23 is housed slidably along the axial direction of the cylindrical body 21. By the movement of the gasket 23 in the distal direction, the drug solution Q in the cylindrical body 21 can be pushed out from the hollow needle 22.

This gasket 23 is an elastic body whose outer shape is a columnar shape. On an outer circumferential part thereof, plural ring-shaped protrusions 231 (three, in the configuration of the diagram) are so formed as to protrude across the whole circumference. The respective protrusions 231 slide with tight contact with an inner circumferential surface of the cylindrical body 21. This keeps liquid-tight performance more surely and allows enhancement in the slidability.

A constituent material of the gasket 23 is not particularly limited. Examples thereof include the following elastic materials: various kinds of rubber materials such as natural rubber, butyl rubber, isoprene rubber, butadiene rubber, styrene-butadiene rubber, and silicone rubber; various kinds of thermoplastic elastomers such as polyurethane series, polyester series, polyamide series, olefin series, and styrene series; and mixtures of them.

The plunger 24 is coupled to the gasket 23 from a proximal side thereof by e.g. screwing. The plunger 24 is to carry out movement operation of the gasket 23 along the axial direction of the cylindrical body 21.

The plunger 24 has a main body portion 241 having an elongated shape, two pressing portions 242 that are so formed as to protrude on a proximal side of the main body portion 241, and two engagement portions 243 that are so formed as to protrude at positions closer to the distal side than the pressing portions 242 of the main body portion 241. The pressing portions 242 and the engagement portions 243 may be formed at positions different from each other in the middle of the axial direction of the main body portion.

The main body portion 241 is formed of a tubular body and a coil spring 4 can be placed inside it.

The two pressing portions 242 are provided at a proximal part of the main body portion 241. These two pressing portions 242 are disposed on the opposite side to each other through the axis of the main body portion 241. As shown in FIGS. 7 and 8, each pressing portion 242 is a part that presses each inside engagement piece 252 of the engagement member 25 outward to deform it.

As shown in FIG. 6, each pressing portion 242 has a plate piece shape and an inclined surface 245 is formed at its distal part. This inclined surface 245 is so inclined that a distance from the axis of the main body portion 241 gradually increases in the proximal direction. This enables the two pressing portions 242 to easily enter the space between the two inside engagement pieces 252 of the engagement member 25 when the plunger 24 moves in the distal direction. Thus, the respective inside engagement pieces 252 can be surely pressed (see FIGS. 7 and 8). The maximum distance L1 between the two pressing portions 242 is set longer than the minimum distance L2 between the two inside engagement pieces 252 in a natural state in which no external force is given (see FIG. 2).

Furthermore, at the proximal part of the main body portion 241, the two engagement portions 243 are provided at a part slightly closer to the distal side than the pressing portions 242. The engagement portions 243 are parts forming a part of the restricting means 7.

These two engagement portions 243 are disposed on the opposite side to each other through the axis of the main body portion 241. Moreover, the respective engagement portions 243 are each a protrusion protruding in a direction perpendicular to a protrusion direction of each of the pressing portions 242.

In each engagement portion 243, an inclined surface 246 inclined as with the inclined surface 245 of the pressing portion 242 is formed.

For such an internal structural body 2, the protector 3 is movably disposed on an outer circumferential side thereof.

As shown in FIG. 6, the protector 3 has a tubular shape. In its tube wall 31, a pair of void parts 32 is formed from a proximal surface 311 to the middle of the longitudinal direction. Furthermore, a distal portion 36 whose outer diameter is set smaller than that of a barrel portion having the void parts 32 is formed closer to the distal side than the void parts 32, and a step part 37 is formed on a proximal side of a distal portion 36. The outer diameter of the distal portion 36 may be set to the same outer diameter as that of the barrel portion having the void parts 32 and the step part 37 may be formed as a protrusion provided outward on the proximal side of the distal portion 36.

Furthermore, two slits 34 having a U-shape in a side view are formed in the tube wall 31 of the protector 3. This "U-shape" is one inverted upside down, i.e. a shape that a distal side is opened and a proximal side is closed. These two slits 34 are disposed opposed to each other through the axis of the protector 3. Furthermore, the parts surrounded by the respective slits 34 each function as the elastically-deformable outside engagement pieces 33. As shown in FIG. 8, the outside engagement pieces 33 can engage with the inside engagement pieces 252 of the internal structural body 2.

By forming the respective outside engagement pieces 33 by the part of the tube wall 31 of the protector 3 in this manner, a structure of the protector 3 can be simplified compared with a case in which the respective outside engagement pieces 33 are formed by a component different from the tube wall 31 for example.

Furthermore, a rim part 351 of a distal opening 35 of the protector 3 serves as an abutting part made to abut against a living body surface when the drug solution Q is administered to a living body by using the liquid injection instrument 1.

A constituent material of the protector 3 is not particularly limited and e.g. a material similar to the constituent material of the cylindrical body 21 and so forth can be used.

Figure 2:
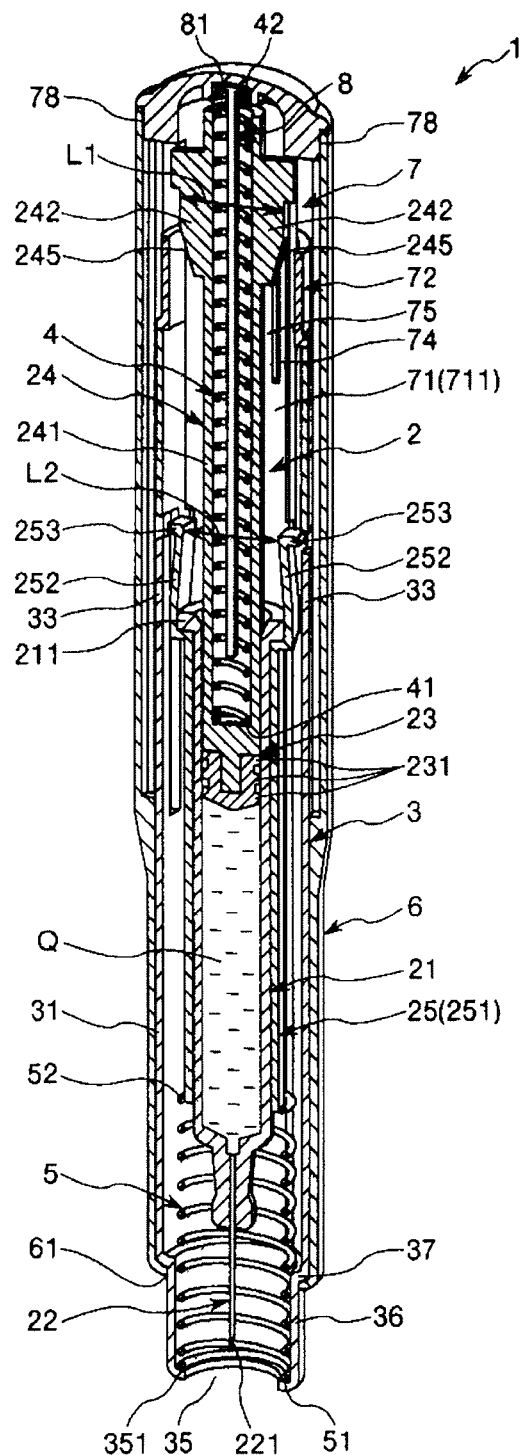
FIG. 2 is a longitudinal-sectional perspective view sequentially showing the actuation state of the liquid injection instrument of the present invention.
Figure 3:
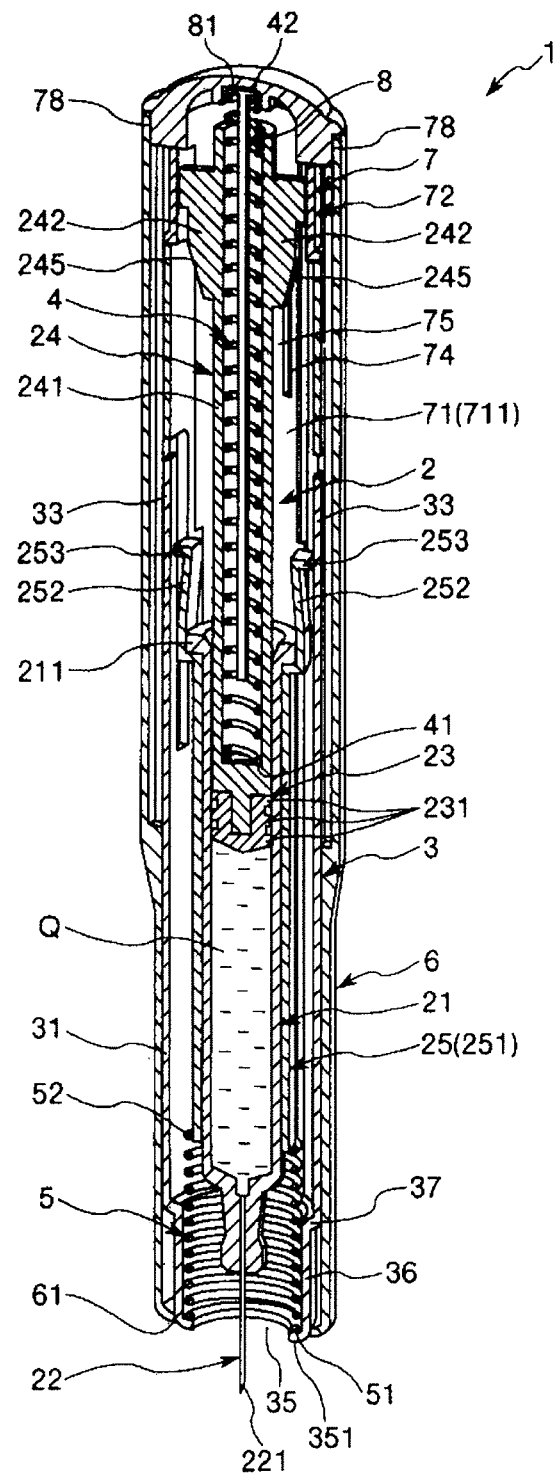
FIG. 3 is a longitudinal-sectional perspective view sequentially showing the actuation state of the liquid injection instrument of the present invention.

Such a protector 3 can take the following four states. A first state is a state in which, as shown in FIG. 2 (FIG. 1), the distal opening 35 of the protector 3 is located closer to the distal side than the needle tip 221 of the hollow needle 22 with the drug solution Q still housed in the cylindrical body 21. A second state is a state in which, as shown in FIG. 3, the needle tip 221 of the hollow needle 22 protrudes from the distal opening 35 of the protector 3 due to the movement of the protector 3 toward the proximal side and the gasket 23 can move in the distal direction. A third state is a state in which, as shown in FIG. 4, the drug solution Q is discharged via the hollow needle 22 due to the movement of the gasket 23 in the distal direction. A fourth state is a state in which, as shown in FIG. 5, the distal opening 35 of the protector 3 is located closer to the distal side than the needle tip 221 of the hollow needle 22 again. Furthermore, in this fourth state, as shown in FIG. 8, the inside engagement pieces 252 of the engagement member 25 are pressed outward by the respective pressing portions 242 of the plunger 24 to engage with the outside engagement pieces 33 of the protector 3. This prohibits the movement of the protector 3 in the proximal direction.

In the liquid injection instrument 1, the coil springs 4 and 5 formed of e.g. stainless steel are incorporated. The coil spring 4 is a component that biases the gasket 23 in the distal direction via the plunger 24 in the third state shown in FIG. 4. The coil spring 5 is a component that biases the protector 3 in the distal direction so that the distal opening 35 of the protector 3 may be located closer to the distal side than the needle tip 221 in the first state shown in FIG. 2, and biases the protector 3 in the distal direction in transition to the fourth state shown in FIG. 5.

The coil spring 4 is set in a compressed state in the plunger 24 of the internal structural body 2. Furthermore, a distal end 41 of the coil spring 4 abuts against a bottom part of the main body portion 241 of the plunger 24 and a proximal end 42 abuts against a flange 81 formed at a proximal part of a buckling prevention member 8 inserted in the coil spring 4 by increasing the diameter. This allows the gasket 23 to be surely biased in the distal direction. The buckling prevention member 8 is an elongated component that prevents buckling, i.e. bending, of the coil spring 4 when this coil spring 4 is contracted.

The coil spring 5 is set in a compressed state at a distal part of the protector 3. The distal part of the internal structural body 2 is inserted in the coil spring 5. Furthermore, a distal end 51 of the coil spring 5 abuts against a proximal side of the rim part 351 of the distal opening 35 of the protector 3 and a proximal end 52 abuts against the engagement member 25. This allows the protector 3 to be surely biased in the distal direction.

The restricting means 7 is so configured as to restrict the movement of the plunger 24 of the internal structural body 2 in the distal direction in the first state and release the restriction on the plunger 24 in the second state. Such restricting means 7 has a first restricting member 71 that has a tubular shape and is provided on the proximal side of the cylindrical body 21 fixedly to this cylindrical body 21 in such a manner that its distal surface abuts against a proximal surface of the cylindrical body 21. The restricting means 7 also has a second restricting member 72 that has a ring shape and is set movably to an outer circumferential side of the first restricting member 71.

As shown in FIGS. 6 and 10, in a tube wall 711 of the tubular first restricting member 71, a pair of void parts 73 is formed from a distal surface 772 to the middle of the longitudinal direction. Furthermore, the pressing portions 242 of the plunger 24 are inserted in the respective void parts 73. Due to this, the engagement portions 243 of the plunger 24 correspond with elastic pieces 75 to be described later in a position about the axis of the plunger 24. In addition, when the plunger 24 moves, this moving plunger 24 is guided by the pressing portions 242 and the void parts 73, so that this movement is smoothly performed.

Moreover, in the tube wall 711 of the first restricting member 71, a pair of slits 74 is formed at positions opposed to each other through the axis of the first restricting member 71. Each slit 74 is composed of three vertical slits arranged in parallel and two lateral slits coupling the adjacent vertical slits to each other. Furthermore, the elastic pieces 75 and 76 that can be elastically deformed are formed at a part surrounded by this slit 74.

The elastic piece 75 can be elastically deformed in such a manner as to be capable of getting close to/away from the engagement portion 243 of the plunger 24. Furthermore, as shown in FIG. 10, a protrusion 751 protruding inward is formed at a proximal part of the elastic piece 75. Moreover, at the proximal part of this protrusion 751, an inclined surface 752 that is so inclined that a distance from the axis of the first restricting member 71 gradually increases in the proximal direction is formed. This inclined surface 752 abuts against the inclined surface 246 of the engagement portion 243 of the plunger 24. Due to this, an outward force is applied to the inclined surface 752 in association with the movement of the plunger 24 in the distal direction. Thus, the elastic piece 75 can be easily deformed outward and get separated from the engagement portion 243.

The second restricting member 72 can move from a restriction position at which its inner circumferential surface is in contact with an outer surface of the elastic piece 75 to a release position located closer to the proximal side than the elastic piece 75. Furthermore, a distal surface of the second restricting member 72 is in contact with a proximal surface of the protector 3. This allows the second restricting member 72 to move in the proximal direction in association with the movement of the protector 3 in the proximal direction.

The elastic piece 76 can be elastically deformed in such a manner as to be capable of getting close to/away from a proximal surface of the second restricting member 72. Furthermore, a protrusion 761 protruding outward is formed at a proximal part of the elastic piece 76. Moreover, at a distal part of this protrusion 761, an inclined surface 762 that is so inclined that a distance from the axis of the first restricting member 71 gradually decreases in the distal direction is formed. Due to this, an inward force is applied to the inclined surface 762 in association with the movement of the second restricting member 72 in the proximal direction. Thus, the elastic piece 76 can be easily deformed inward and get separated from the proximal surface of the second restricting member 72.

In the first state, the elastic piece 75 gets close to the engagement portion 243 and the inclined surface 752 of the protrusion 751 engages with the inclined surface 246 of the engagement portion 243. Furthermore, the second restricting member 72 exists at the restriction position and prevents the elastic piece 75 from being outward deformed to get separated from the engagement portion 243. Moreover, the protrusion 761 of the elastic piece 76 engages with the proximal surface of the second restricting member 72 and prevents the unintended movement of the second restricting member 72 in the proximal direction. Due to this, the engagement state between the elastic piece 75 and the engagement portion 243 is kept and the movement of the plunger 24 in the distal direction is surely prevented.

In transition to the second state, the elastic piece 76 is easily deformed inward in association with the movement of the protector 3 in the proximal direction. Thereby, the engagement with the proximal surface of the second restricting member 72 is released and the second restricting member 72 moves in the proximal direction to the release position. This releases the keeping of the engagement state between the elastic piece 75 and the engagement portion 243. Furthermore, the elastic piece 75 is easily deformed outward, which releases the engagement between the elastic piece 75 and the engagement portion 243 and makes it possible for the plunger 24 to move in the distal direction.

Moreover, the biasing force of the coil spring 4 is set to sufficient magnitude to outward deform the elastic piece 75 via the engagement portion 243 and release the engagement between the elastic piece 75 and the engagement portion 243 when the second restricting member 72 exists at the release position. This can surely push ahead the plunger 24 in the distal direction by the coil spring 4.

A constituent material of each of the first restricting member 71 and the second restricting member 72 is not particularly limited. For example, a material similar to the constituent material of the cylindrical body 21 and so forth or polyacetal can be used.

On the outer circumferential side of the protector 3, the cylindrical grip member 6 grasped when the liquid injection instrument 1 is used is set. Grasping the grip member 6 makes the liquid injection instrument 1 easy to use.

Furthermore, the grip member 6 is disposed concentrically with the protector 3 and fixedly supports the internal structural body 2 inside it in such a manner that the needle tip 221 of the hollow needle 22 protrudes from a distal opening 61. In addition, it supports the protector 3 in such a manner that the protector 3 can move relative to the internal structural body 2 along the axial direction thereof. Due to this, in the first state, the protector 3 is biased in the distal direction by the coil spring 5 and a large part of the distal portion 36 protrudes from the distal opening 61 of the grip member 6. Thus, the needle tip 221 is located closer to the proximal side than the distal opening 35 of the protector 3. In the second state and the third state, the protector 3 moves to a position closer to the proximal side than the position of the first state and thereby the needle tip 221 protrudes from the distal opening 35 of the protector 3. In the fourth state, a large part of the distal portion 36 of the protector 3 protrudes from the distal opening 61 of the grip member 6 again due to the biasing force of the coil spring 5. This allows the needle tip 221 to be located closer to the proximal side than the distal opening 35 of the protector 3.

As shown in FIGS. 6 and 11, at an inner circumferential part of the grip member 6, two grooves 63 are formed along its longitudinal direction. These grooves 63 are disposed opposed to each other through the axis of the grip member 6. Furthermore, when the outside engagement pieces 33 of the protector 3 are pushed and expanded outward by the pressing portions 242 of the plunger 24 as described later, the outside engagement pieces 33 escape into (enter) the grooves 63 and thus the plunger 24 can smoothly move.

As shown in FIGS. 9 and 11, at the inner circumferential part of the grip member 6, four ribs 62 are so formed as to protrude along its longitudinal direction at positions different from those of the grooves 63. The respective two of the ribs 62 are inserted in each void part 32 of the protector 3. Due to this, when the protector 3 moves along the axial direction of the grip member 6, the protector 3 is guided by the respective ribs 62 and thus the movement is smoothly performed. Furthermore, the guide portions 254 of the engagement member 25 are inserted between the respective two of the ribs 62 inserted in each void part 32. Due to this, furthermore the protector 3 and the engagement member 25 are aligned with the grip member 6, so that the inside engagement pieces 252, the outside engagement pieces 33, and the grooves 63 correspond with each other in a position about the axis of the grip member 6.

In addition, two protrusions 78 that are so formed as to protrude at a proximal part of the first restricting member 71 are inserted in proximal parts of the respective grooves 63. This aligns the first restricting member 71 with the grip member 6. Therefore, the void parts 73 of the first restricting member 71 correspond with the grooves 63 in the position about the axis of the grip member 6. Moreover, the pressing portions 242 of the plunger 24 correspond with the inside engagement pieces 252 in the position about the axis of the grip member 6. In addition, the first restricting member 71 is fixed to the grip member 6 by a method such as fitting, fusion (thermal fusion, ultrasonic fusion, high-frequency fusion, etc.), or bonding (bonding by adhesive or solvent) in such a form that the protrusions 78 are inserted in the grooves 63 of the grip member 6.

Furthermore, an inner diameter of the distal opening 61 of the grip member 6 is reduced. The step part 37 of the protector 3 abuts against a rim part of this diameter-reduced distal opening 61. This prevents separation of the protector 3 from a distal end of the grip member 6. In addition, between the respective two of the ribs 62, in which the guide portions 254 of the engagement member 25 are inserted, a protrusion 65 protruding inward is formed in the middle of the longitudinal direction of the grip member 6. A distal surface of the guide portion 254 abuts against a proximal surface of this protrusion 65. Due to this, the engagement member 25 and the cylindrical body 21 are clamped by the protrusions 65 of the grip member 6 and the first restricting member 71 fixed to the grip member 6 to thereby be fixed in the grip member 6.

A distance along the longitudinal direction from the distal opening 61 of the grip member 6 to the proximal surfaces of the protrusions 65 is longer than the length of the distal portion 36 of the protector 3 along the axial direction. Due to this, when the protector 3 moves in the proximal direction to become the second state, the guide portions 254 of the engagement member 25 do not abut against the distal portion 36. Thus, the movement distance of the protector 3 is sufficiently ensured.

As shown in FIGS. 6, 9, and 11, in the grip member 6, two slits 64 are formed along its longitudinal direction at positions closer to the proximal side than the protrusions 65 and between the respective two of the ribs 62, in which the guide portions 254 of the engagement member 25 are inserted. Furthermore, due to the ribs 62 and the protrusions 65 of the grip member 6, the slits 64 correspond with penetration holes 255 formed in a penetrating manner in the guide portions 254 of the engagement member 25 in the position about the axis of the grip member 6 and in the longitudinal direction. This makes it possible to check the state of the drug solution Q in the cylindrical body 21 from the outside through the slit 64 and the penetration hole 255.

A constituent material of the grip member 6 is not particularly limited and e.g. a material similar to the constituent material of the cylindrical body 21 and so forth can be used.

Figure 1:
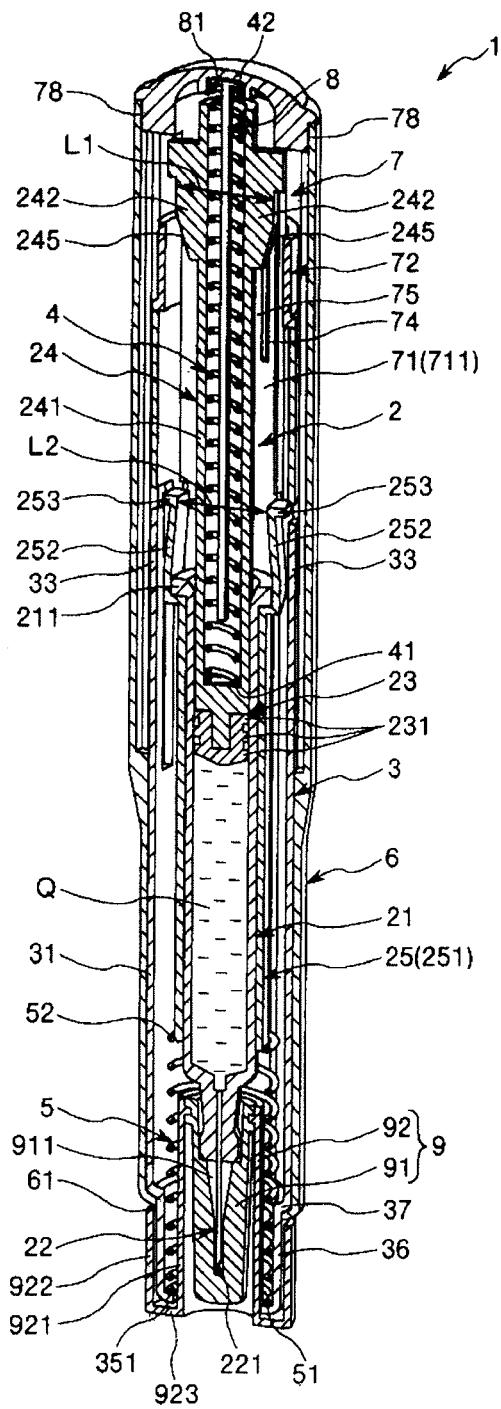
FIG. 1 is a longitudinal-sectional perspective view sequentially showing an actuation state of a liquid injection instrument of the present invention.

Furthermore, as shown in FIG. 1, a freely-removable cap 9 is put at the distal part of the liquid injection instrument 1 that has not yet been used. The cap 9 is composed of a needle tip protecting member 91 covering the needle tip 221 and a cover member 92 covering the needle tip protecting member 91.

The needle tip protecting member 91 is formed of a pillar-shaped component having a hollow part 911 corresponding to the outer shape of the distal part of the internal structural body 2. The needle tip 221 can be housed in this hollow part 911 and protected.

The cover member 92 is disposed on an outer circumferential side of the needle tip protecting member 91. The cover member 92 has a double-tube structure having an inner tube 921 and an outer tube 922. Furthermore, distal parts of the inner tube 921 and the outer tube 922 are coupled to each other by a ring-shaped coupler 923.

At a proximal inner circumferential part of the inner tube 921 of the cover member 92 and a proximal outer circumferential part of the needle tip protecting member 91, e.g. recession and projection (groove and protrusion) that engage with each other are formed. This fixes the needle tip protecting member 91 to the cover member 92 and allows the cover member 92 to be pulled in the distal direction collectively with the needle tip protecting member 91. The cap 9 can be removed by this pulling operation.

Furthermore, the movement of the cover member 92 in the proximal direction is limited by the rim part of the distal opening 61 of the grip member 6 and a proximal surface of the outer tube 922 of the cover member 92. This limits the movement of the protector 3 in the proximal direction. Due to this, the first state, in which the distal opening 35 of the protector 3 is located closer to the distal side than the needle tip 221, is kept until the time of injection.

Next, a use method of the liquid injection instrument 1 will be described with reference to FIGS. 1, 2, 3, 4 (7), 5 (8), and 6.

[1] The liquid injection instrument 1 shown in FIG. 1, which has not yet been used, is prepared. In this liquid injection instrument 1, the drug solution Q of a sufficient degree for administration is filled.

Furthermore, because the cap 9 is put for the liquid injection instrument 1, this cap 9 is removed.

[2] As shown in FIG. 2, the liquid injection instrument 1 from which this cap 9 is removed is in the first state.

Furthermore, the distal opening 35 of the protector 3 is located closer to the distal side than the needle tip 221 of the hollow needle 22 of the internal structural body 2 and this state is kept by the coil spring 5. In addition, the second restricting member 72 is located at the restriction position to keep the engagement state between the elastic pieces 75 of the first restricting member 71 and the engagement portions 243 of the plunger 24. This surely prevents the movement of the plunger 24 in the distal direction (see FIG. 6).

[3] Next, the user grasps the grip member 6 of the liquid injection instrument 1 with a single hand and, against the biasing force of the coil spring 5, presses the rim part 351 of the distal opening 35 of the protector 3 against a target site of a living body surface. At this time, the protector 3 receives a reaction force from the living body surface and moves in the proximal direction. This causes the liquid injection instrument 1 to enter the second state shown in FIG. 3. In this second state, the needle tip 221 of the hollow needle 22 protrudes from the distal opening 35 of the protector 3. This allows puncturing of the living body surface by the needle tip 221.

Moreover, in association with the movement of the protector 3 in the proximal direction, the second restricting member 72 is also pushed up in the proximal direction to move to the release position. This releases the keeping of the engagement state between the elastic pieces 75 of the first restricting member 71 and the engagement portions 243 of the plunger 24. Thus, the elastic pieces 75 are easily deformed outward by the biasing force of the coil spring 4 and the engagement between the elastic pieces 75 and the engagement portions 243 is released. This biasing force of the coil spring 4 is transmitted to the gasket 23 via the plunger 24, which provides the state in which this gasket 23 can move in the distal direction together with the plunger 24.

[4] Then, the liquid injection instrument 1 enters the third state shown in FIG. 4 and the gasket 23 moves in the distal direction. Thereby, the drug solution Q is discharged via the hollow needle 22 to be administered to the living body. The gasket 23 can move until abutting against the bottom part of the cylindrical body 21. Thus, almost all of the drug solution Q is discharged.

Furthermore, as shown in FIG. 7, the pressing portions 242 of the plunger 24 that moves in the distal direction press and expand the outside engagement pieces 33 of the protector 3 outward collectively with the inside engagement pieces 252 of the engagement member 25.

[5] Next, when the liquid injection instrument 1 is moved away from the living body surface, the protector 3 moves in the distal direction due to the biasing force of the coil spring 5 and the liquid injection instrument 1 enters the fourth state shown in FIG. 5. In this fourth state, the distal opening 35 of the protector 3 is located closer to the distal side than the needle tip 221 of the hollow needle 22 again.

Furthermore, as shown in FIG. 8, in this fourth state, proximal ends 331 of the outside engagement pieces 33 of the protector 3 can get over the claws 253 of the inside engagement pieces 252 of the engagement member 25 and return to the original shape, i.e. the natural state. At this time, the claws 253 of the inside engagement pieces 252 of the engagement member 25, which remain pressed and deformed outward by the pressing portions 242 of the plunger 24, engage with the proximal ends 331 of the outside engagement pieces 33 of the protector 3, whose shape is restored. This engagement prohibits the protector 3 from moving in the proximal direction again. This prevents the hollow needle 22 from protruding from the distal opening 35 of the protector 3 again. Thus, accidental puncturing of a finger or the like by the hollow needle 22 after the use of the liquid injection instrument 1 can be surely prevented.

By the simple operation, i.e. pressing the liquid injection instrument 1 against the living body surface and then pulling it up in this manner, the series of operation until the injection (administration) of the drug solution Q can be carried out. Therefore, the liquid injection instrument 1 is excellent in the operability of the drug solution injection operation.

Furthermore, with the liquid injection instrument 1, the user itself can control the pressing speed and the pressing force when this liquid injection instrument 1 is pressed against the living body surface. This can reduce fear when the living body surface of the user is punctured by the hollow needle 22.

Moreover, the liquid injection instrument 1 does not have such a configuration that button operation is carried out like the conventional liquid injection instrument and therefore its structure is simple. Thus, e.g. reduction in a cost in manufacturing of the liquid injection instrument 1 and the number of components can be achieved.

Although the liquid injection instrument of the present invention is explained above about the embodiment shown in the diagrams, the present invention is not limited thereto and the respective parts configuring the liquid injection instrument can be replaced by ones that can exert similar functions and have any configuration. Furthermore, any constituent object may be added.

INDUSTRIAL APPLICABILITY

A liquid injection instrument of the present invention includes an internal structural body having a cylindrical body that has a cylindrical shape and has an inner cavity part in which a liquid is housed, a hollow needle that is disposed at a distal part of the cylindrical body, communicates with the cylindrical body, and has a sharp needle tip at a distal end, a gasket slidable in the cylindrical body, and a plunger that is coupled to the gasket and carries out a movement operation of the gasket along an axial direction of the cylindrical body. The liquid injection instrument further includes a protector that is disposed on an outer circumferential side of the internal structural body movably relative to the internal structural body along the axial direction, and has a tubular shape and a distal opening. The protector is capable of taking a first state in which the liquid still remains housed in the cylindrical body and the distal opening of the protector is located closer to the distal side than the needle tip, a second state in which the needle tip protrudes from the distal opening due to a movement of the protector toward a proximal side and the gasket is movable in a distal direction, a third state in which the liquid is discharged via the hollow needle due to a movement of the gasket in the distal direction, and a fourth state in which the distal opening is located closer to the distal side than the needle tip again. The protector has an outside engagement piece that is provided in a tube wall of the protector and is elastically deformed. The cylindrical body has an inside engagement piece that is provided at a proximal part of the cylindrical body, engages with the outside engagement piece in the fourth state, and is elastically deformed. The plunger has a pressing portion that presses and deforms the inside engagement piece outward in the fourth state. In the fourth state, the inside engagement piece is pressed outward by the pressing portion to engage with the outside engagement piece, so that the movement of the protector in a proximal direction is prohibited by the engagement.

Therefore, e.g. provision of a button for the puncturing operation and so forth can be omitted. Thus, the structure can be simplified.

Furthermore, the internal structural body can be prohibited from moving in the distal direction again after the puncturing. Thus, the needle tip of the hollow needle is prevented from protruding from the distal opening of the protector again. Accordingly, accidental puncturing of a finger or the like by the needle tip after the use of the liquid injection instrument can be surely prevented. Therefore, the liquid injection instrument is excellent in the operability of the liquid injection operation (particularly prevention of accidental puncturing after the use) and has industrial applicability.

The invention claimed is:
1. A liquid injection instrument comprising:
an internal structural body having
a cylindrical body that has a cylindrical shape and has an inner cavity part in which a liquid is housed,
a hollow needle that is disposed at a distal part of the cylindrical body, communicates with the cylindrical body, and has a sharp needle tip at a distal end,
a gasket that is slidable in the cylindrical body, and
a plunger that is coupled to the gasket and carries out a movement operation of the gasket along an axial direction of the cylindrical body; and
a protector that is disposed on an outer circumferential side of the internal structural body movably relative to the internal structural body along the axial direction, and has a tubular shape and a distal opening;
wherein the protector is capable of taking
a first state in which the liquid still remains housed in the cylindrical body and the distal opening of the protector is located closer to a distal side than the needle tip,
a second state in which the needle tip protrudes from the distal opening of the protector due to a movement of the protector toward a proximal side and the gasket is movable in a distal direction,
a third state in which the liquid is discharged via the hollow needle due to a movement of the gasket in the distal direction, and
a fourth state in which the distal opening of the protector is located closer to the distal side than the needle tip again,
wherein the protector has an outside engagement piece that is provided in a tube wall of the protector and is elastically deformed,
the cylindrical body has an inside engagement piece that is provided at a proximal part of the cylindrical body, engages with the outside engagement piece in the fourth state, and is elastically deformed, and
the plunger has a pressing portion that presses and deforms the inside engagement piece outward in the fourth state,
wherein in the third state, the pressing portion of the plunger moved in the distal direction presses and expands the outside engagement piece outward collectively with the inside engagement piece, and
wherein in the fourth state, the outside engagement piece returns to an original shape, and the inside engagement piece remains pressed and deformed outward by the pressing portion to engage directly with the outside engagement piece, so that the movement of the protector in a proximal direction is prohibited by the engagement.

2. The liquid injection instrument according to claim 1, wherein the protector has a slit having a U-shape in a side view of the protector, the slit is formed in the tube wall of the protector, and a part surrounded by the slit functions as the outside engagement piece.

3. The liquid injection instrument according to claim 1, wherein the inside engagement piece is so formed as to protrude in the proximal direction at the proximal part of the cylindrical body and has a claw that is so formed as to protrude outward at a proximal end of the inside engagement piece, and wherein the claw engages with the outside engagement piece.

4. The liquid injection instrument according to claim 1, wherein the plunger is formed of an elongated member, and wherein the pressing portion is a part that is so formed as to protrude in the middle of an axial direction of the plunger, and has an inclined surface that is so inclined that a distance from an axis of the plunger gradually increases in the proximal direction.

5. The liquid injection instrument according to claim 1, further comprising restricting means that restricts a movement of the plunger in the distal direction in the first state and releases the restriction on the plunger in the second state.

6. The liquid injection instrument according to claim 5, wherein the plunger is formed of an elongated member, wherein the restricting means has
- a protrusion that is so formed as to protrude at a position different from a position of the pressing portion in the middle of an axial direction of the plunger,
- a first restricting member that is provided fixedly to the cylindrical body and includes an elastic piece elastically deformed in such a manner as to be capable of getting close to and away from the protrusion, and
- a second restricting member that moves to a restriction position at which the elastic piece gets close to and engages with the protrusion and an engagement between the elastic piece and the protrusion is kept, and moves from the restriction position to a release position at which the elastic piece is capable of getting away from the protrusion, and wherein the second restricting member is located at the restriction position in the first state, and moves to the release position in association with the movement of the protector in the proximal direction in transition to the second state.

7. The liquid injection instrument according to claim 6, further comprising a first biasing member that biases the gasket in the distal direction via the plunger in the third state, wherein a biasing force of the first biasing member is set to such a magnitude as to release the engagement between the elastic piece and the protrusion when the second restricting member exists at the release position.

8. The liquid injection instrument according to claim 1, further comprising a second biasing member that biases the protector in the distal direction so that the distal opening of the protector is located closer to the distal side than the needle tip in the first state, and biases the protector in the distal direction so that the distal opening of the protector is located closer to the distal side than the needle tip again in transition to the fourth state.

9. The liquid injection instrument according to claim 1, further comprising a cylindrical grip member that has a cylindrical shape and a distal opening, and is disposed concentrically with the protector, wherein the grip member fixedly supports, inside the grip member, the internal structural body in such a manner that the needle tip protrudes from the distal opening of the grip member, and the grip member supports the protector movably relative to the internal structure body along the axial direction.

* * * * *